(12) United States Patent
Liu et al.

(10) Patent No.: US 12,138,090 B2
(45) Date of Patent: Nov. 12, 2024

(54) INFORMATION PROCESSING METHOD, MEDICAL IMAGE DIAGNOSTIC APPARATUS, AND INFORMATION PROCESSING SYSTEM FOR DETECTING A QUIESCENT CARDIAC PHASE

(71) Applicant: CANON MEDICAL SYSTEMS CORPORATION, Tochigi (JP)

(72) Inventors: Chih-chieh Liu, Vernon Hills, IL (US); Jian Zhou, Vernon Hills, IL (US); Qiulin Tang, Vernon Hills, IL (US); Liang Cai, Vernon Hills, IL (US); Zhou Yu, Vernon Hills, IL (US)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 300 days.

(21) Appl. No.: 17/875,051

(22) Filed: Jul. 27, 2022

(65) Prior Publication Data
US 2024/0032877 A1    Feb. 1, 2024

(51) Int. Cl.
*A61B 6/03* (2006.01)
*A61B 6/00* (2024.01)
*A61B 6/50* (2024.01)
*G01N 23/046* (2018.01)

(52) U.S. Cl.
CPC ............ *A61B 6/032* (2013.01); *A61B 6/4417* (2013.01); *A61B 6/54* (2013.01); *G01N 23/046* (2013.01); *A61B 6/503* (2013.01)

(58) Field of Classification Search
CPC ......... A61B 6/032; A61B 6/4417; A61B 6/54; A61B 6/503; A61B 6/488; A61B 6/541
See application file for complete search history.

(56) References Cited

U.S. PATENT DOCUMENTS

2023/0148985 A1* 5/2023 Kanno .................... A61B 6/545
378/62

FOREIGN PATENT DOCUMENTS

| JP | 2007-37782 | 2/2007 |
|---|---|---|
| JP | 2009-517113 | 4/2009 |
| JP | 2010-025702 | 2/2010 |
| JP | 4533670 | 6/2010 |
| JP | 4731476 | 4/2011 |
| JP | 2013-236744 | 11/2013 |
| JP | 5619707 | 9/2014 |

* cited by examiner

*Primary Examiner* — David P Porta
*Assistant Examiner* — Casey Bryant
(74) *Attorney, Agent, or Firm* — Oblon, McClelland, Maier & Neustadt, L.L.P.

(57) ABSTRACT

An information processing method controls a CT scanner such that the method includes, but is not limited to, determining an X-ray irradiation period from an electrocardiogram acquired from an electrocardiography device attached to a living object to be imaged, by processing the electrocardiogram at multiple different cardiac phases; performing, by controlling a CT gantry including and rotatably supporting an X-ray source and an X-ray detector, a diagnostic CT scan in the determined X-ray irradiation period, of at least a part of the heart region, to obtain a CT image; and causing a display unit to display the obtained CT image. The method can be performed at least by an information processing apparatus including processing circuitry and/or computer instructions stored in a non-transitory computer readable storage medium for performing the method.

12 Claims, 10 Drawing Sheets

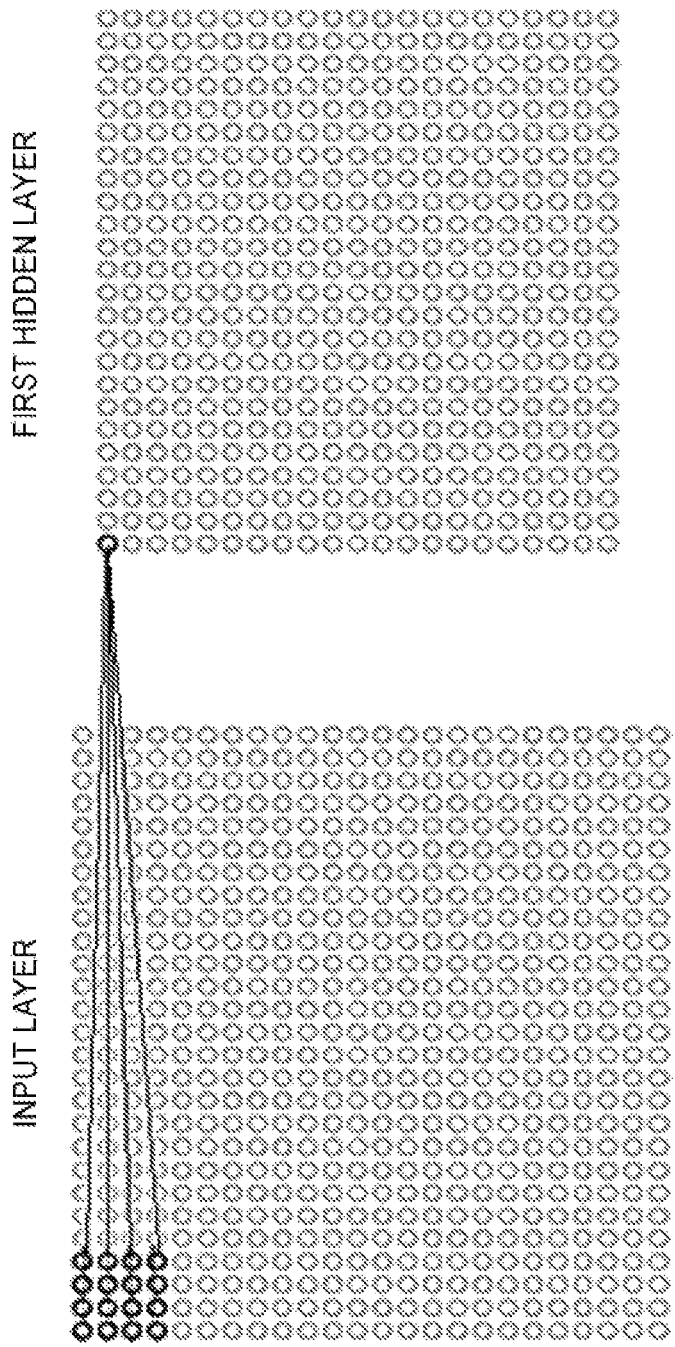

INFORMATION PROCESSING METHOD, MEDICAL IMAGE DIAGNOSTIC APPARATUS, AND INFORMATION PROCESSING SYSTEM FOR DETECTING A QUIESCENT CARDIAC PHASE

FIELD

Embodiments described herein relate generally to an information processing method, a medical image diagnostic apparatus, and an information processing system.

BACKGROUND

A medical image (e.g., a cardiac image) acquired from a subject by a medical image diagnostic apparatus (e.g., an x-ray computed tomography (CT) apparatus) may include motion which can detract from image quality. Moreover, motion in coronary CT angiography (CCTA) tends to be rapid and non-uniform deformation occurs between individuals.

Some echocardiogram-based approaches have been proposed to select quiescent cardiac phase by calculating cross-correlation between 2D image frames at different time points without ECG, which is an indirect measure of spatial information of the heart. However, the presence of ultrasound transducers in CT field-of-view (FOV) can cause significant image artifacts. Also, the accuracy of selecting phase can vary with ultrasound FOV location.

BRIEF DESCRIPTION OF THE DRAWINGS

FIG. 3C illustrates a general convolutional neural network having multiple connections between an input layer and a first hidden layer as part of a training process according to an exemplary embodiment described below.

DETAILED DESCRIPTION

An information processing method of an embodiment is a method of controlling a CT scanner including, but not limited to, determining an X-ray irradiation period from an electrocardiogram acquired from an electrocardiography device attached to a living object to be imaged, by processing the electrocardiogram at multiple different cardiac phases; performing, by controlling a CT gantry including and rotatably supporting an X-ray source and an X-ray detector, a diagnostic CT scan in the determined X-ray irradiation period, of at least a part of the heart region, to obtain a CT image; and causing a display unit to display the obtained CT image.

The disclosure herein also describes an information processing apparatus including processing circuitry and/or computer instructions stored in a non-transitory computer readable storage medium for performing the above-noted method.

Hereinafter, with reference to the accompanying drawings, an embodiment of an information processing method, a medical image diagnostic apparatus, and an information processing system will be described in detail.

In the present embodiment, X-ray CT will be described as an example of a medical image diagnostic modality. That is, in the present embodiment, an information processing method of information acquired by imaging performed by the X-ray CT will be described.

Figure 1:
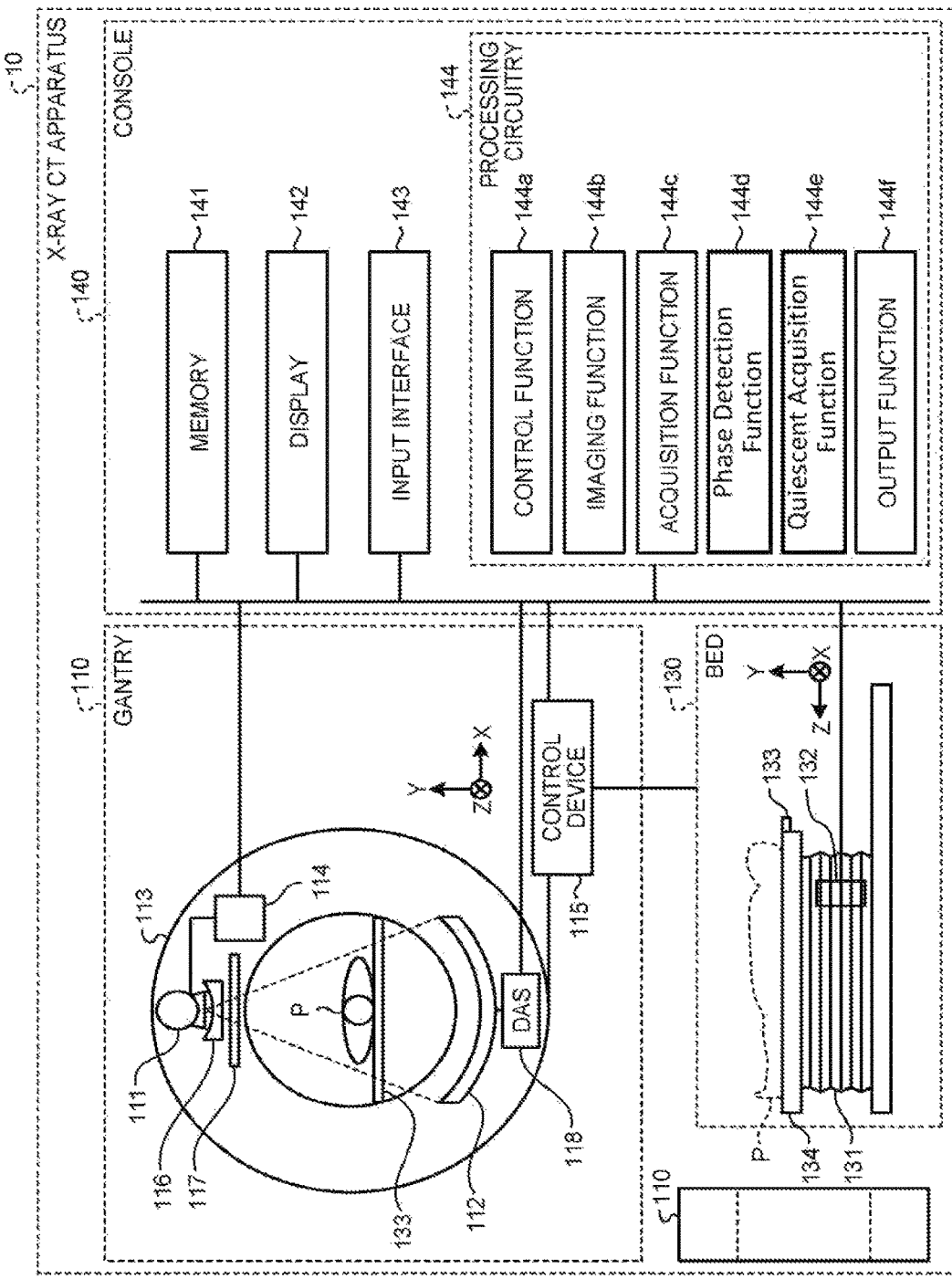
FIG. 1 is a block diagram of an exemplary configuration of an X-ray CT apparatus imaging a person as a subject according to an exemplary embodiment described below.

The X-ray CT is implemented, for example, in an X-ray CT apparatus 10 illustrated in FIG. 1. FIG. 1 is a block diagram illustrating an example of a configuration of the X-ray CT apparatus 10 according to a first embodiment. For example, the X-ray CT apparatus 10 has a gantry 110, a bed 130, and a console 140.

In FIG. 1, it is assumed that the longitudinal direction of a rotating shaft of a rotating frame 113 or a tabletop 133 of the bed 130 in a non-tilted state is a Z axis direction. Furthermore, it is assumed that an axial direction orthogonal to the Z axis direction and horizontal to a floor surface is an X axis direction. Furthermore, it is assumed that an axial direction orthogonal to the Z axis direction and perpendicular to the floor surface is a Y axis direction. Note that FIG. 1 illustrates the gantry 110 drawn from a plurality of directions for convenience of description and the X-ray CT apparatus 10 has one gantry 110.

The gantry 110 includes an X-ray tube 111, an X-ray detector 112, the rotating frame 113, an X-ray high voltage device 114, a control device 115, a wedge 116, a collimator 117, and a data acquisition system (DAS) 118.

The X-ray tube 111 is a vacuum tube having a cathode (filament) that generates thermoelectrons and an anode (target) that generates X-rays in response to a collision of thermoelectrons. The X-ray tube 111 emits the thermoelectrons toward the anode from the cathode by the application of a high voltage from the X-ray high voltage device 114, thereby generating the X-rays to be emitted to a subject P.

The X-ray detector 112 detects the X-rays emitted from the X-ray tube 111 and passed through the subject P, and outputs a signal corresponding to the dose of the detected X-rays to the DAS 118. The X-ray detector 112, for example, includes a plurality of detection element arrays in which a plurality of detection elements are arranged in a channel direction (channel direction) along one arc centered on a focal point of the X-ray tube 111. The X-ray detector 112, for example, has a structure in which the detection element arrays with the detection elements arranged in the channel direction are arranged in a row direction (slice direction and row direction).

For example, the X-ray detector 112 is an indirect conversion type detector having a grid, a scintillator array, and a photosensor array. The scintillator array has a plurality of scintillators. Each of the scintillators has a scintillator crystal that outputs light with a photon quantity corresponding to an incident X-ray dose. The grid has an X-ray shielding plate that is disposed on the surface of the scintillator array on an X-ray incident side and absorbs scatted X-rays. The grid may also be referred to as a collimator (a one-dimensional collimator or a two-dimensional collimator). The photosensor array has a function of converting light into an electrical signal corresponding to the amount of light from the scintillator, and has, for example, photosensors such as photodiodes. Note that the X-ray detector 112 may be a direct conversion type detector having a semiconductor element that converts the incident X-rays into electrical signals.

The rotating frame 113 is an annular frame that supports the X-ray tube 111 and the X-ray detector 112 so as to face each other and rotates the X-ray tube 111 and the X-ray detector 112 by the control device 115. For example, the rotating frame 113 is a casting made of aluminum. Note that the rotating frame 113 can further support the X-ray high voltage device 114, the wedge 116, the collimator 117, the DAS 118 and the like, in addition to the X-ray tube 111 and the X-ray detector 112. Moreover, the rotating frame 113 can further support various configurations not illustrated in FIG. 1. Hereinafter, in the gantry 110, the rotating frame 113 and a part, which rotationally moves with the rotating frame 113, are also referred to as a rotating part.

The X-ray high voltage device 114 has electric circuitry such as a transformer and a rectifier and has a high voltage generation device that generates a high voltage to be applied to the X-ray tube 111 and an X-ray control device that controls an output voltage corresponding to the X-rays generated by the X-ray tube 111. The high voltage generation device may be a transformer type device or an inverter type device. Note that the X-ray high voltage device 114 may be provided on the rotating frame 113, or may also be provided on a fixed frame (not illustrated).

The control device 115 has processing circuitry having a central processing unit (CPU) and the like, and a driving mechanism such as a motor and an actuator. The control device 115 receives input signals from an input interface 143 and controls the operations of the gantry 110 and the bed 130. For example, the control device 115 controls the rotation of the rotating frame 113, the tilt of the gantry 110, the operation of the bed 130, and the like. As an example, as control for tilting the gantry 110, the control device 115 rotates the rotating frame 113 around an axis parallel to the X axis direction based on information on an input inclination angle (tilt angle). Note that the control device 115 may be provided in the gantry 110 or may also be provided in the console 140.

The wedge 116 is an X-ray filter for adjusting the dose of the X-rays emitted from the X-ray tube 111. Specifically, the wedge 116 is an X-ray filter that attenuates the X-rays emitted from the X-ray tube 11 such that the X-rays emitted from the X-ray tube 111 to the subject P have a predetermined distribution. For example, the wedge 116 is a wedge filter or a bow-tie filter and is manufactured by processing aluminum and the like to have a predetermined target angle and a predetermined thickness.

The collimator 117 is a lead plate and the like for narrowing down the emission range of the X-rays having transmitted through the wedge 116 and forms a slit by a combination of a plurality of lead plates and the like. Note that the collimator 117 may also be referred to as an X-ray diaphragm. Furthermore, although FIG. 1 illustrates a case where the wedge 116 is disposed between the X-ray tube 111 and the collimator 117, the collimator 117 may be disposed between the X-ray tube 111 and the wedge 116. In such a case, the wedge 116 attenuates the X-rays, which are emitted from the X-ray tube 111 and whose emission range is limited by the collimator 117, by allowing the X-rays to pass therethrough.

The DAS 118 acquires X-ray signals detected by each detector element included in the X-ray detector 112. For example, the DAS 118 has an amplifier that performs an amplification process on electrical signals output from each detector element and an A/D converter that converts the electrical signals to digital signals and generates detection data. The DAS 118 is implemented by, for example, a processor.

The data generated by the DAS 118 is transmitted from a transmitter having a light emitting diode (LED) provided on the rotating frame 113 to a receiver having a photodiode provided on a non-rotating part (for example, a fixed frame and the like and not illustrated in FIG. 1) of the gantry 110 by optical communication and is transmitted to the console 140. The non-rotating part is, for example, a fixed frame and the like that rotatably supports the rotating frame 113. Note that the data transmission method from the rotating frame 113 to the non-rotating part of the gantry 110 is not limited to the optical communication and may adopt any non-contact type data transmission method or a contact type data transmission method.

The bed 130 is a device that places and moves the subject P to be scanned and includes a pedestal 131, a couch driving device 132, the tabletop 133, and a support frame 134. The pedestal 131 is a casing that supports the support frame 134 so as to be movable in a vertical direction. The couch driving device 132 is a driving mechanism that moves the tabletop 133, on which the subject P is placed, in a long axis direction of the tabletop 133 and includes a motor, an actuator and the like. The tabletop 133 provided on the upper surface of the support frame 134 is a plate on which the subject P is placed, Note that the couch driving device 132 may also move the support frame 134 in the long axis direction of the tabletop 133 in addition to the tabletop 133.

The console 140 has a memory 141, a display 142, the input interface 143, and processing circuitry 144. Although the console 140 is described as a separate body from the gantry 110, the gantry 110 may include the console 140 or a part of each component of the console 140.

The memory 141 is implemented by, for example, a semiconductor memory element such as a random access memory (RAM) and a flash memory, a hard disk, an optical disk, and the like. For example, the memory 141 stores a computer program for circuitry included in the X-ray CT apparatus 10 to perform its functions. Furthermore, the memory 141 stores various information obtained by imaging the subject P. Furthermore, the memory 141 stores a noise reduction processing model generated by the processing circuitry 144 to be described below. Note that the memory 141 may be implemented by a server group (cloud) connected to the X-ray CT apparatus 10 via a network.

The display 142 displays various information. For example, the display 142 displays an image obtained during an identified quiescent period. Furthermore, for example, the display 142 displays a graphical user interface (GUI) for receiving various instructions, settings, and the like from a user via the input interface 143. For example, the display 142 is a liquid crystal display or a cathode ray tube (CRT) display. The display 142 may be a desktop type display, or may be composed of a tablet terminal and the like capable of wirelessly communicating with the body of the X-ray CT apparatus 10.

Although the X-ray CT apparatus 10 is described as including the display 142 in FIG. 1, the X-ray CT apparatus 10 may include a projector instead of or in addition to the display 142. Under the control of the processing circuitry 144, the projector can perform projection onto a screen, a wall, a floor, the body surface of the subject P, and the like. As an example, the projector can also perform projection onto any plane, object, space, and the like by projection mapping.

The input interface 143 receives various input operations from a user, converts the received input operations into electrical signals, and outputs the electrical signals to the processing circuitry 144. For example, the input interface 143 is implemented by a mouse, a keyboard, a trackball, a switch, a button, a joystick, a touch pad for performing an input operation by touching an operation surface, a touch screen in which a display screen and a touch pad are integrated, non-contact input circuitry using an optical sensor, voice input circuitry, and the like. Note that the input interface 143 may be composed of a tablet terminal and the like capable of wirelessly communicating with the body of the X-ray CT apparatus 10. Furthermore, the input interface 143 may be circuitry that receives an input operation from a user by motion capture. As an example, the input interface 143 can receive a user's body movement, line of sight, and the like as an input operation by processing a signal acquired via a tracker or an image collected for a user. Furthermore, the input interface 143 is not limited to one including physical operation parts such as a mouse and a keyboard. For example, an example of the input interface 143 includes electric signal processing circuitry which receives an electric signal corresponding to an input operation from an external input device separately provided from the X-ray CT apparatus 10 and outputs the electric signal to the processing circuitry 144.

The processing circuitry 144 controls the overall operation of the X-ray CT apparatus 10 by performing a control function 144a, an imaging function 144b, an acquisition function 144c, and an output function 144f.

For example, the processing circuitry 144 reads a computer program corresponding to the control function 144a from the memory 141 and executes the read computer program, thereby controlling various functions, such as the imaging function 144b, the acquisition function 144c, and the output function 144f, based on various input operations received from a user via the input interface 143.

Furthermore, for example, the processing circuitry 144 reads a computer program corresponding to the imaging function 144b from the memory 141 and executes the read computer program, thereby imaging the subject P. For example, the imaging function 144b controls the X-ray high voltage device 114 to supply the X-ray tube 111 with a high voltage. With this, the X-ray tube 111 generates X-rays to be emitted to the subject P. Furthermore, the imaging function 144b controls the couch driving device 132 to move the subject P into an imaging port of the gantry 110. Furthermore, the imaging function 144b adjusts the position of the wedge 116 and the opening degree and position of the collimator 117, thereby controlling the distribution of the X-rays emitted to the subject P. Furthermore, the imaging function 144b controls the control device 115 to rotate the rotating part. Furthermore, while the imaging is performed by the imaging function 144b, the DAS 118 acquires X-ray signals from the respective detection elements in the X-ray detector 112 and generates detection data.

Furthermore, the imaging function 144b performs pre-processing on the detection data output from the DAS 118. For example, the imaging function 144b performs pre-processing, such as logarithmic transformation processing, offset correction processing, inter-channel sensitivity correction processing, and beam hardening correction, on the detection data output from the DAS 118. Note that the data subjected to the pre-processing is also described as raw data. Furthermore, the detection data before the pre-processing and the raw data subjected to the pre-processing are also collectively described as projection data.

Furthermore, for example, the processing circuitry 144 reads a computer program corresponding to the acquisition function 144c from the memory 141 and executes the read computer program, thereby acquiring noise data based on imaging a subject P and acquiring synthesized subject data based on first subject projection data obtained by imaging the subject P and combining with the noise data. Furthermore, for example, the processing circuitry 144 reads a computer program corresponding to the output function 144f from the memory 141 and executes the read computer program, thereby outputting an image obtained during an identified quiescent period. Details of processing performed by the acquisition function 144c, and the output function 144f will be described below.

In the X-ray CT apparatus 10 illustrated in FIG. 1, the respective processing functions are stored in the memory 141 in the form of the computer programs executable by a computer. The processing circuitry 144 is a processor that performs a function corresponding to each computer program by reading and executing the computer program from the memory 141. In other words, the processing circuitry 144 having read the computer program has a function corresponding to the read computer program.

Note that, in FIG. 1, it has been described that the control function 144a, the imaging function 144b, the acquisition function 144c, and the output function 144f are implemented by the single processing circuitry 144, but the processing circuitry 144 may be configured by combining a plurality of independent processors, and each processor may be configured to perform each function by executing each computer program. Furthermore, each processing function of the processing circuitry 144 may be performed by being appropriately distributed or integrated into a single circuit or a plurality of processing circuits.

Furthermore, the processing circuitry 144 may also perform the functions by using a processor of an external device connected via the network. For example, the processing circuitry 144 reads and executes the computer program corresponding to each function from the memory 141 and uses, as computation resources, a server group (cloud)

connected to the X-ray CT apparatus 10 via the network, thereby performing each function illustrated in FIG. 1.

Furthermore, although FIG. 1 illustrates only the single memory 141, the X-ray CT apparatus 10 may include a plurality of physically separated memories. For example, the X-ray CT apparatus 10 may separately include, as the memory 141, a memory that stores a computer program required when circuitry included in the X-ray CT apparatus 10 performs its function, and a memory that stores various information obtained by imaging the subject P.

Figure 2:
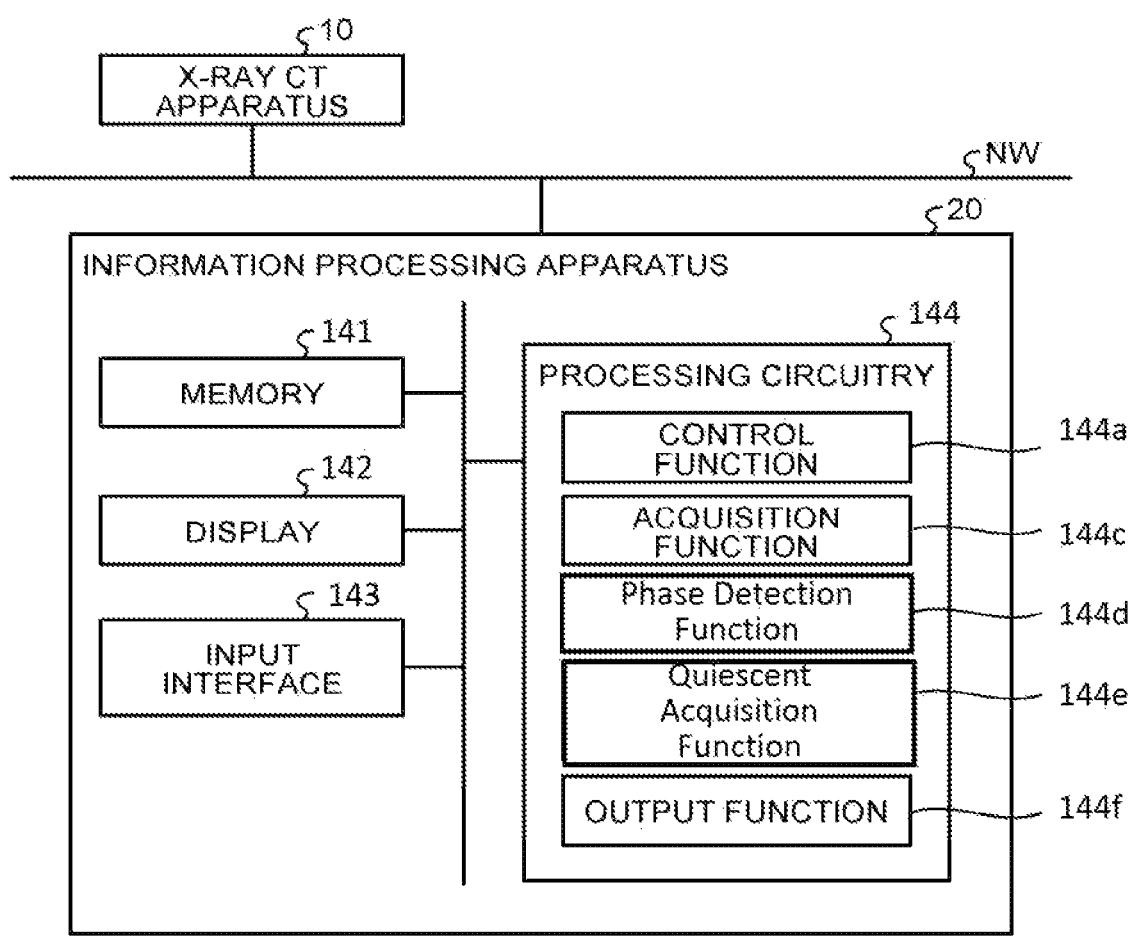
FIG. 2 is a block diagram of an exemplary configuration of information processing apparatus connected to an X-ray CT apparatus according to another exemplary embodiment described below.

Hereinafter, this point will be described with reference to FIG. 2. FIG. 2 is a block diagram illustrating an example of a configuration of an information processing system 1 according to a second embodiment. For example, the information processing system 1 includes an X-ray CT apparatus 10 and an information processing apparatus 20 as illustrated in FIG. 2. The X-ray CT apparatus 10 and the information processing apparatus 20 are connected to each other via a network NW.

Note that the location where the X-ray CT apparatus 10 and the information processing apparatus 20 are installed is arbitrary as long as they can be connected via the network NW. For example, the X-ray CT apparatus 10 and the information processing apparatus 20 may be installed within facilities different from each other, That is, the network NW may be a local network closed within the facility or a network via the Internet. Furthermore, communication between the X-ray CT apparatus 10 and the information processing apparatus 20 may be performed via another apparatus such as an image storage apparatus, or may be directly performed without using another apparatus. An example of such an image storage apparatus includes a picture archiving and communication system (PACS) server, for example.

The X-ray CT apparatus 10 illustrated in FIG. 2 has the same configuration as that of the X-ray CT apparatus 10 illustrated in FIG. 1. However, the processing circuitry 144 of the X-ray CT apparatus 10 illustrated in FIG. 2 may or may not have such functions as the acquisition function 144c and the output function 144f. Furthermore, although FIG. 2 illustrates the X-ray CT apparatus 10 as an example of a medical image diagnostic apparatus, the information processing system 1 may include a medical image diagnostic apparatus different from the X-ray CT apparatus 10. Furthermore, the information processing system 1 may include a plurality of medical image diagnostic apparatuses.

The information processing apparatus 20 performs various processes based on data acquired by the X-ray CT apparatus 10, For example, as illustrated in FIG. 2, the information processing apparatus 20 includes a memory 141, a display 142, an input interface 143, and processing circuitry 144. The display 142 can be configured similarly to the aforementioned display 142 in the apparatus 10. The information processing apparatus 20 may include a projector instead of or in addition to the display 142.

The input interface 143 can be configured similarly to the aforementioned input interface 143 of the X-ray CT apparatus 10. For example, the input interface 143 receives various input operations from a user, converts the received input operations into electrical signals, and outputs the electrical signals to the processing circuitry 144.

The processing circuitry 144 controls the overall operation of the information processing apparatus 20 by performing a control function 144a, an acquisition function 144c, and an output function 144f. For example, the control function 144a controls various functions such as the acquisition function 144c and the output function 144f based on the various input operations received from the user via the input interface 143. The acquisition function 144c is a function corresponding to the acquisition function 144c of the X-ray CT apparatus 10. The output function 144f is a function corresponding to the output function 144f of the X-ray CT apparatus 10.

In the information processing apparatus 20 illustrated in FIG. 2, respective processing functions are stored in the memory 141 in the form of computer programs that can be executed by a computer. The processing circuitry 144 is a processor that reads and executes the computer programs from the memory 141, thereby performing functions corresponding to the computer programs. In other words, the processing circuitry 144 having read the computer programs has the functions corresponding to the read computer programs. Furthermore, each processing function of the processing circuitry 144 may be performed by being appropriately distributed or integrated into a single processing circuit or a plurality of processing circuits. Furthermore, the processing circuitry 144 may also perform the functions by using a processor of an external device connected via the network NW. For example, the processing circuitry 144 reads and executes the computer programs corresponding to the functions from the memory 141 and uses, as computation resources, a server group (cloud) connected to the information processing apparatus 20 via the network NW, thereby performing the functions illustrated in FIG. 2.

Furthermore, in FIG. 1, it has been described that the single memory 141 stores the computer programs corresponding to the respective processing functions of the processing circuitry 144. Furthermore, in FIG. 2, it has been described that the single memory 144 stores the computer programs corresponding to the respective processing functions of the processing circuitry 144. However, the embodiment is not limited thereto. For example, a plurality of memories 141 may be arranged in a distributed manner, and the processing circuitry 144 may be configured to read corresponding computer programs from the individual memories 141. Furthermore, instead of storing the computer programs in the memory 141, the computer programs may be directly incorporated in the circuit of the processor. In such a case, the processor reads and executes the computer programs incorporated in the circuit to perform functions thereof.

Each component of each apparatus according to the aforementioned embodiment is functionally conceptual and does not necessarily need to be physically configured as illustrated in the drawings. That is, the specific form of distribution and integration of each apparatus is not limited to that illustrated in the drawing and all or some thereof can be functionally or physically distributed and integrated in arbitrary units according to various loads, usage conditions, and the like. Moreover, all or some of the processing functions performed by each apparatus may be performed by the CPU and the computer programs that are analyzed and executed by the CPU, or may be performed as a wired logic-based hardware.

Furthermore, the information processing method described in the aforementioned embodiment can be implemented by executing an information processing program prepared in advance on a computer such as a personal computer and a workstation. The information processing program can be distributed via a network such as the Internet. Furthermore, the information processing program can be executed by being recorded on a non-transitory computer readable recording medium such as a hard disk, a flexible disk (FD), a CD-ROM, an MO, and a DVD, and being read from the recording medium by the computer.

Figure 3A:
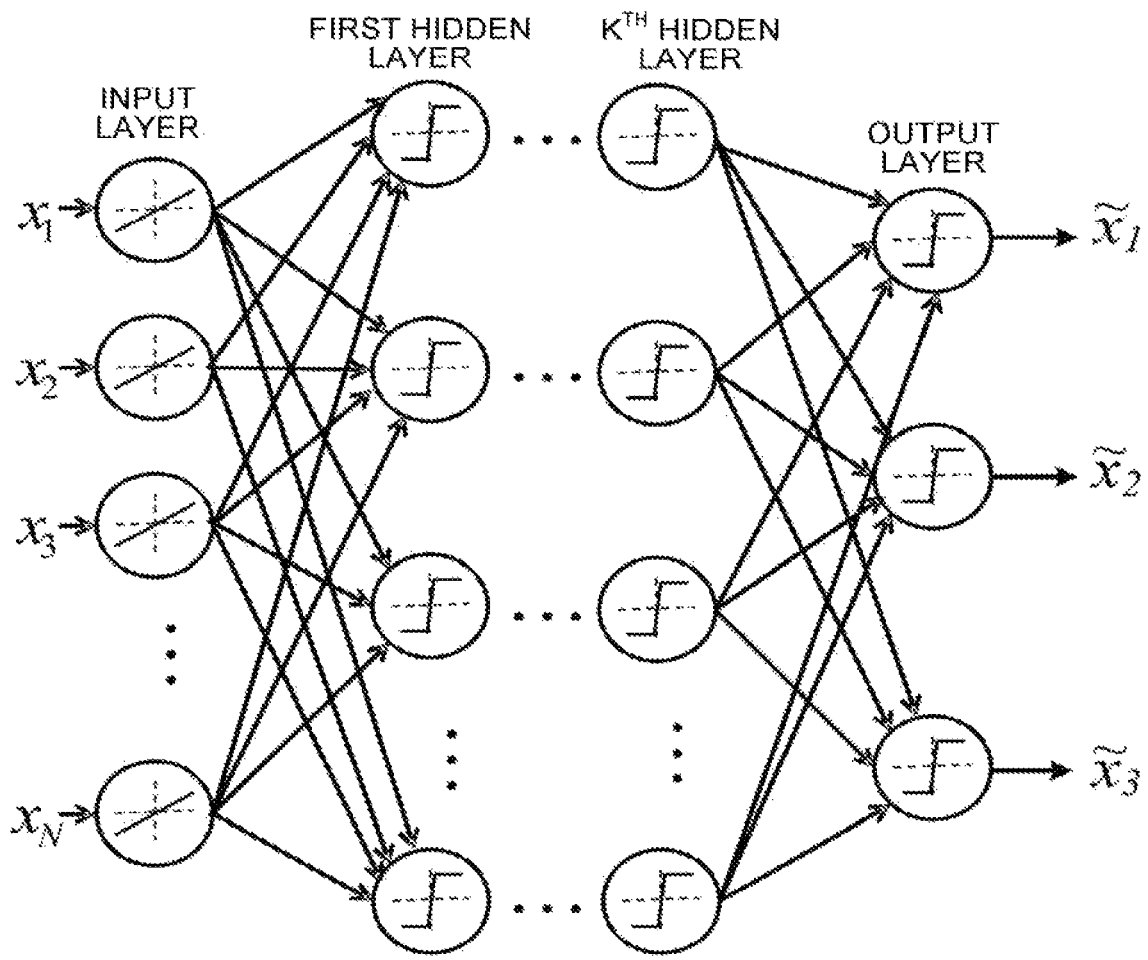
FIG. 3A illustrates a general neural network to be trained according to an exemplary embodiment described below.
Figure 3B:
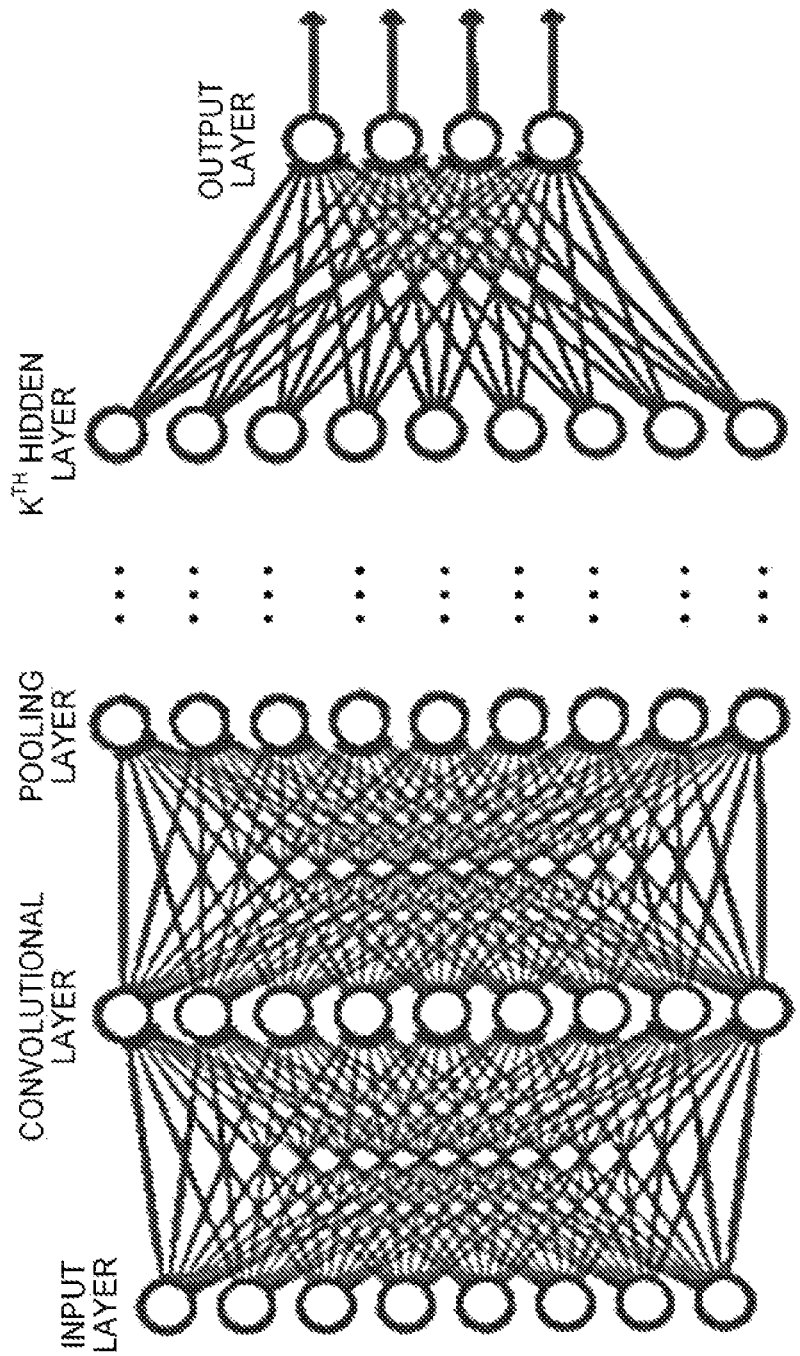
FIG. 3B illustrates a general convolutional neural network to be trained according to an exemplary embodiment described below.

FIG. 3A to FIG. 3C illustrate a training process according to an exemplary embodiment described below. More specifically, FIG. 3A illustrates a general artificial neural network (ANN) having n inputs, a $K^{th}$ hidden layer, and three outputs. Each layer of the ANN is made up of nodes (also called neurons), and each node performs a weighted sum of the inputs to produce an output and compares the result of the weighted sum with a threshold. ANNs make up a class of functions for which members of the class are acquired by varying thresholds, connection weights, or specifics of an architecture such as the number of nodes and/or their connectivity. The nodes in the ANN may be referred to as neurons (or neuronal nodes), and the neurons can have inter-connections between different layers of the ANN system. For example, the ANN has more than three layers of neurons and has as many output neurons x to N as input neurons, wherein N is the number of pixels in the reconstructed image. Synapses (that is, connections between neurons) store values called "weights" (also interchangeably referred to as "coefficients" or "weighting coefficients") that manipulate data in calculations. The outputs of the ANN depend on three types of parameters: (i) An interconnection pattern between different layers of neurons, (ii) A learning process for updating weights of the interconnections, and (iii) An activation function that converts a neuron's weight input to its output activation.

Mathematically, a neuron's network function m(x) is defined as a composition $n_i$ (x) of other functions, which can further be defined as a composition of other functions. This can be conveniently represented as a network structure, with arrows depicting dependencies between variables, as illustrated in FIG. 3A. For example, the ANN can use a nonlinear weighted sum, wherein m $(x)=K(\Sigma_i w_i n_i(x))$, where K (commonly referred to as an "activation function") is a predetermined coefficient such as a sigmoidal function, a hyperbolic tangent function, and a rectified linear unit (ReLU).

In FIG. 3A (and similarly in FIG. 31), the neurons (that is, nodes) are depicted by circles around a threshold function. In the non-limiting example illustrated in FIG. 3A, the inputs are depicted by circles around a linear function and the arrows indicate directed connections between neurons. In a specific embodiment, the ANN is a feedforward network as exemplified in FIG. 3A and FIG. 3B (for example, it can be represented as a directed acyclic graph).

The ANN operates to achieve a specific task, such as identification of a quiescent period for obtaining a CT image, by searching within the class of a function F to learn, using a set of observation results, to find an element $m^*(m^* \in F)$ which solves the specific task in some optimal criteria (for example, a stopping criteria). For example, in a specific embodiment, this can be achieved by defining a cost function $C:F \rightarrow R$, such as for an optimal solution expressed by the following Equation (1)(that is, no solution having a cost less than the cost of the optimal solution).

$$C(m^*) \leq C(m) \forall m \in F \quad (1)$$

In Equation (1), m* is the optimal solution. The cost function C is a measure of how far away a particular solution is from an optimal solution to a problem to be solved (for example, an error). Learning algorithms iteratively search through the solution space to fine a function with the smallest possible cost. In a specific embodiment, the cost is minimized over a sample of the data (that is, the training data).

FIG. 3B illustrates a non-limiting example in which the ANN is a DCNN. The DCNN is a type of ANN having beneficial properties for image processing. The DCNN uses a feedforward ANN in which a connectivity pattern between neurons can represent convolutions in image processing. For example, the DCNN can be used for image processing optimization by using multiple layers of small neuron collections that process portions of an input image, called receptive fields. The outputs of these collections can then be tiled so that they overlap, to achieve a better representation of the original image. This processing pattern can be repeated over multiple layers having alternating convolution and pooling layers. Note that FIG. 3B illustrates an example of a fully connected (full connect) network that defines a node of a succeeding layer by using all the nodes of a preceding layer. This example only illustrates an example of a deep neural network (DNN). It is common for the DCNN to form a loosely connected (partial connect) network that defines a node of a succeeding layer by using some of the nodes of a preceding layer.

FIG. 3C illustrates an example of a 5×5 kernel being applied to map values from an input layer representing a two-dimensional image to a first hidden layer which is a convolution layer. The kernel maps respective 5×5 pixel regions to corresponding neurons of the first hidden layer. Following after the convolution layer, the DCNN can include local and/or global pooling layers that combine the outputs of neuron clusters in the convolution layers. Moreover, in a specific embodiment, the DCNN can also include various combinations of convolutional and fully connected layers, with pointwise nonlinearity applied at the end of or after each layer.

The DCNN has several advantages for image processing. To reduce the number of free parameters and improve generation, a convolution operation on small regions of input is introduced. One significant advantage of the specific embodiment of the DCNN is the use of shared weights in the convolution layer, that is, filters (weight banks) used as coefficients for each pixel in the layer are the same. Such significant advantages reduce a memory footprint and improve performance. Compared to other image processing methods, the DCNN advantageously uses relatively little pre-processing. This means that the DCNN is responsible for learning manually designed filters in traditional algorithms. The lack of dependence on prior knowledge and human effort in designing features is a major advantage for the DCNN.

In the supervised learning, a set of training data is acquired, and the network is iteratively updated to reduce errors, such that output of the partially trained network improves to match a desired/target output using a cost function The cost function can use a mean-squared error to optimize an average squared error. In the case of multilayer perceptrons (MLP) neural network, a backpropagation algorithm can be used for training the network by minimizing the mean-squared-error-based cost function using a gradient descent method. In general, DL networks can be trained using any of numerous algorithms for training neural network models (for example, applying optimization theory or statistical estimation).

For example, the optimization method used in training artificial neural networks can use some form of gradient descent, using backpropagation to compute actual gradients. This is done by taking the derivative of the cost function with respect to network parameters and then changing those parameters in a gradient-related direction. The backpropagation algorithm may be a steepest descent method (for example, with variable learning rate, with variable learning rate and momentum, and resilient backpropagation), a quasi-Newton method (for example, Broyden-Fletcher-Goldfarb-Shanno, one step secant, and Levenberg-Marquardt), or a conjugate gradient method (for example, Fletcher-Reeves update, Polak-Ribiére update, Powell-Beale restart, and scaled conjugate gradient). Moreover, evolutionary methods, such as gene expression programming, simulated annealing, expectation-maximization, non-parametric methods, and particle swarm optimization, can also be used for training the DCNN.

When the cost function (for example, the error) has a local minimum different from the global minimum, a robust stochastic optimization process is beneficial to find the global minimum of the cost function. An example of an optimization method for finding a local minimum can be a Nelder-Mead simplex method, a gradient descent method, a Newton's method, a conjugate gradient method, a shooting method, and one of other known local optimization methods. There are also many known methods for finding global minima, including generic algorithms, simulated annealing, exhaustive searches, interval methods, and other related deterministic, stochastic, heuristic, and metaheuristic method. Any of these methods can be used to optimize the weights/coefficients of the DCNN. Moreover, neural networks can also be optimized using a backpropagation method.

Using a CT apparatus 10 (in FIGS. 1 and 2), an emitter 111 can be used to obtain first lower-radiation dose image data during a first scan of a patient as would be performed during a scout scan while obtaining ECG data (from an electrocardiography device) during the imaging. It further is possible to utilize a CT apparatus with more than one paired emitter and detector. For example, two emitters, each with their own detector, can be arranged at intersecting angles (e.g., 45 degrees from each other or 90 degrees from each other), and images can be obtained in quick succession from each to image the heart from multiple angles nearly simultaneously and correlated to an acquired ECG signal. In yet another embodiment, a fast acquisition 3D scout scan can be used to obtain the images used to find a quiescent phase of a heart such that the quiescent phase is found more uniformly across the whole heart as opposed to in a 2D slice (or 2D slices).

Figure 4:
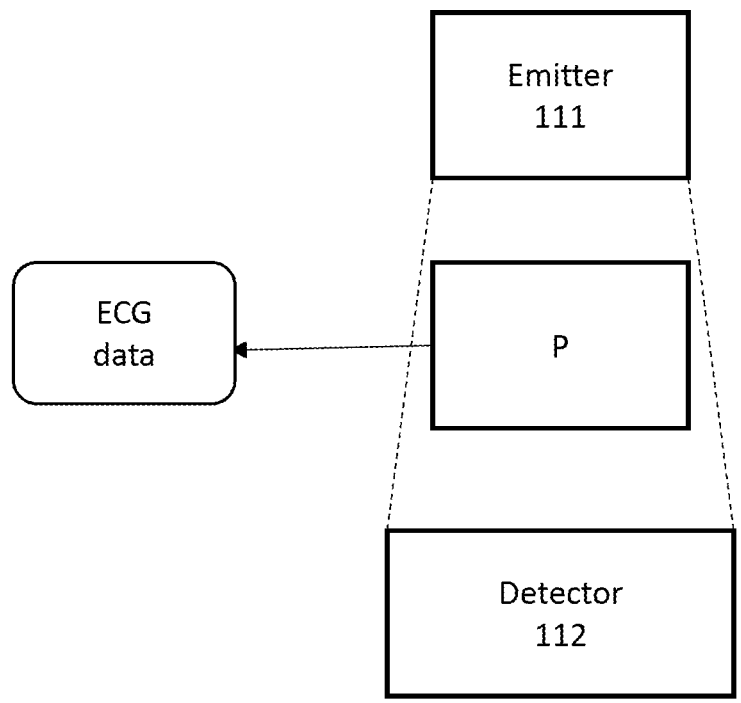
FIG. 4 illustrates an x-ray emitter and an x-ray emitter and detector imaging a patient at multiple times during an R-R interval.
Figure 5:
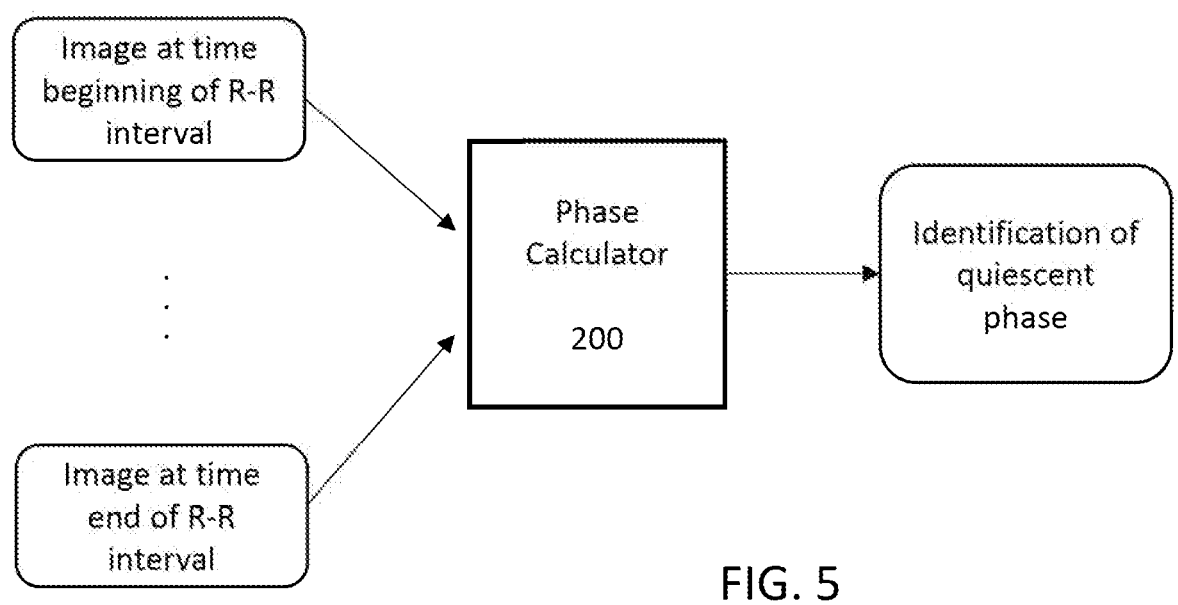
FIG. 5 illustrates a phase calculator for determining a quiescent cardiac phase by processing multiple scout CT images acquired, from a scout CT scan prior to a diagnostic scan, over multiple different cardiac phases.

In one embodiment, CT-compatible leads of an ECG are placed on the chest of the patient inside the gantry. The process is generally shown in FIG. 4, and images (e.g., 60 anterior-posterior (AP) images) over a full R-R interval (e.g., 0.8-1.3 seconds) are obtained without moving a gantry on which the patient is positioned. (Such a scout scan generally will be in addition to a positioning scan (that is either 2D or 3D) that determines a proper position for the patient on the gantry and that typically is performed just proceeding the scout scans described herein.) Having obtained the ECG data and the first lower-radiation dose image data during the first scan, the method and system described herein can be used to determine an X-ray irradiation period associated with the ECG data by processing the ECG data and multiple first CT images acquired, from the first CT scan, at multiple different cardiac phases. For example, as shown in FIG. 5, a phase calculator 200 can be used to identify a quiescent phase (and optionally a duration) of the quiescent phase. In one embodiment, the phase calculator 200 calculates cardiac motion-related metrics based on the first CT scans within individual R-R intervals associated with the electrocardiogram and approximates the duration as a fixed percentage (e.g., 3%) of the interval (centered at the determined quiescent phase).

Figure 6:
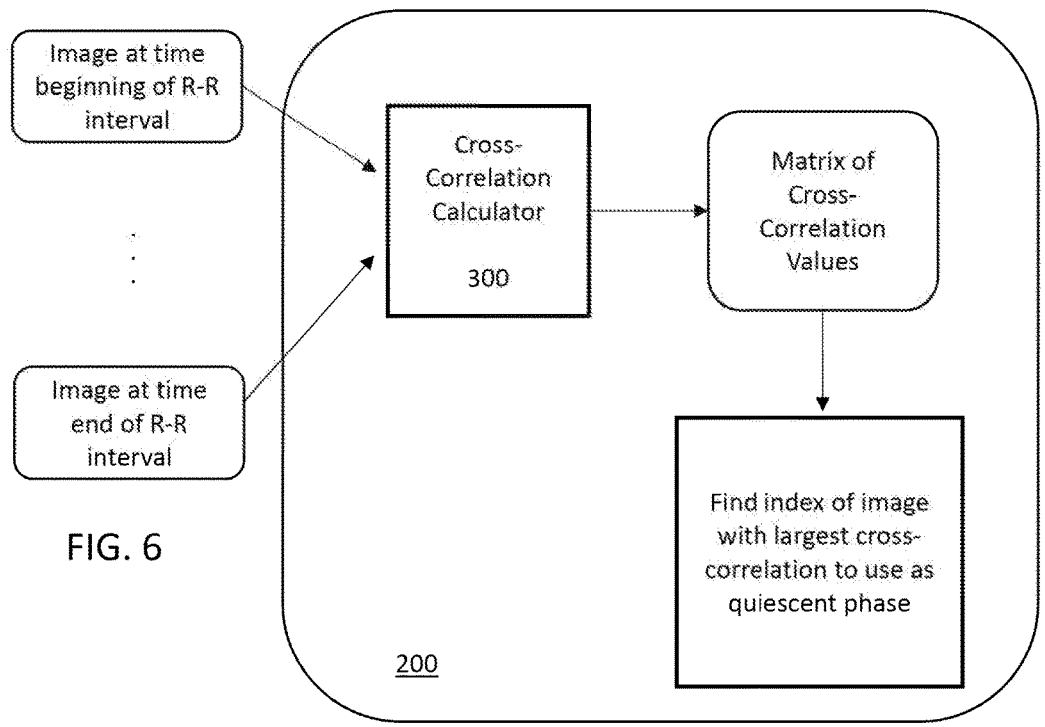
FIG. 6 illustrates a cross correlator acting as phase calculator of FIG. 5.

As is shown in FIG. 6, as part of a phase calculator 200, in a first embodiment of an analytical process for identifying the quiescent phase, a cross-correlation between each of the "n" 2D scout views (e.g., 60 scout views) at different phases is performed to produce a matrix of cross-correlation values (thereby producing (n*(n−1))/2 correlation values). From the matrix, a quiescent phase is determined by selecting the corresponding view having the highest correlation value in the matrix. In an alternate embodiment, cross-correlations are only performed for adjacent images, and the quiescent phase is determined by selecting the corresponding view having the highest correlation value in the list of adjacent correlation values. The cross-correlations described above can be performed either sequentially or in parallel (e.g., across multiple threads, cores, processors or computers).

Figure 7:
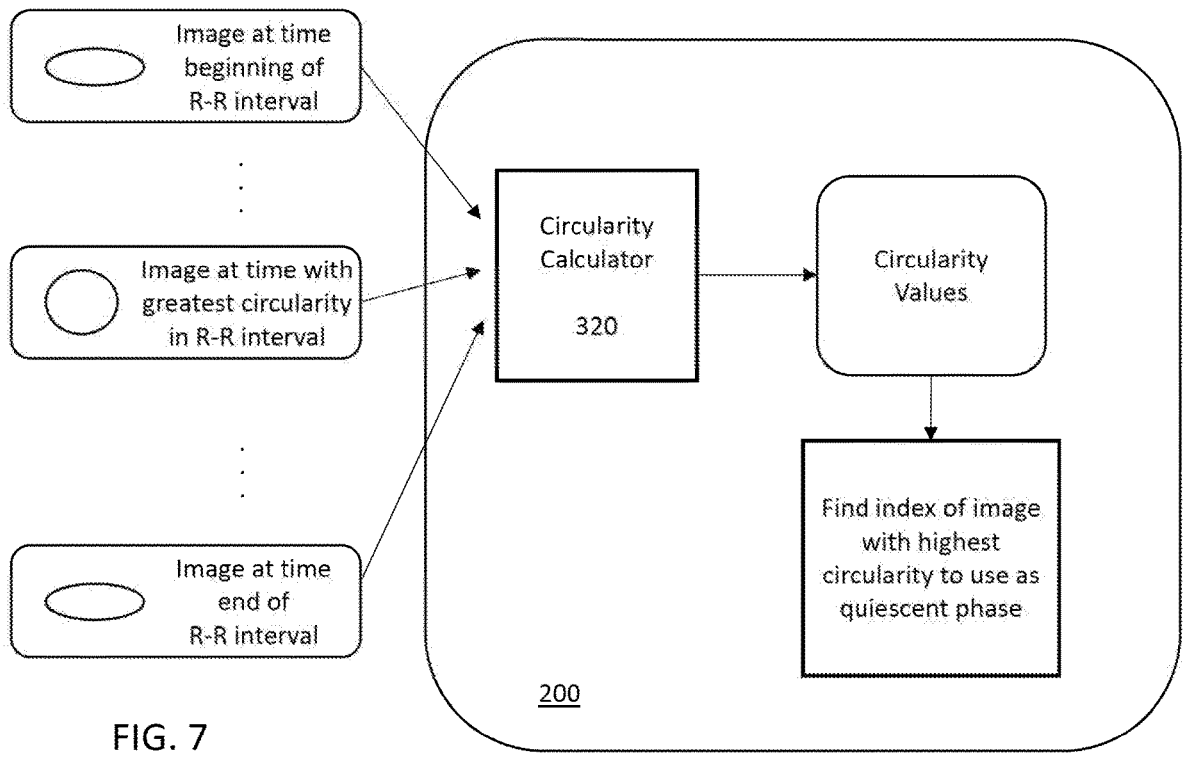
FIG. 7 illustrates a circularity calculator acting as phase calculator of FIG. 5.

As shown in FIG. 7, in a second embodiment, a quiescent phase is determined using a circularity score. In that embodiment, circularity scores of one or more coronary arteries in the 2D scout views at different phases are determined, and the quiescent phase is selected to correspond to the 2D scout scan with the highest circularity score. The calculations of circularity scores described above can be performed either sequentially or in parallel (e.g., across multiple threads, cores, processors or computers).

Figure 8:
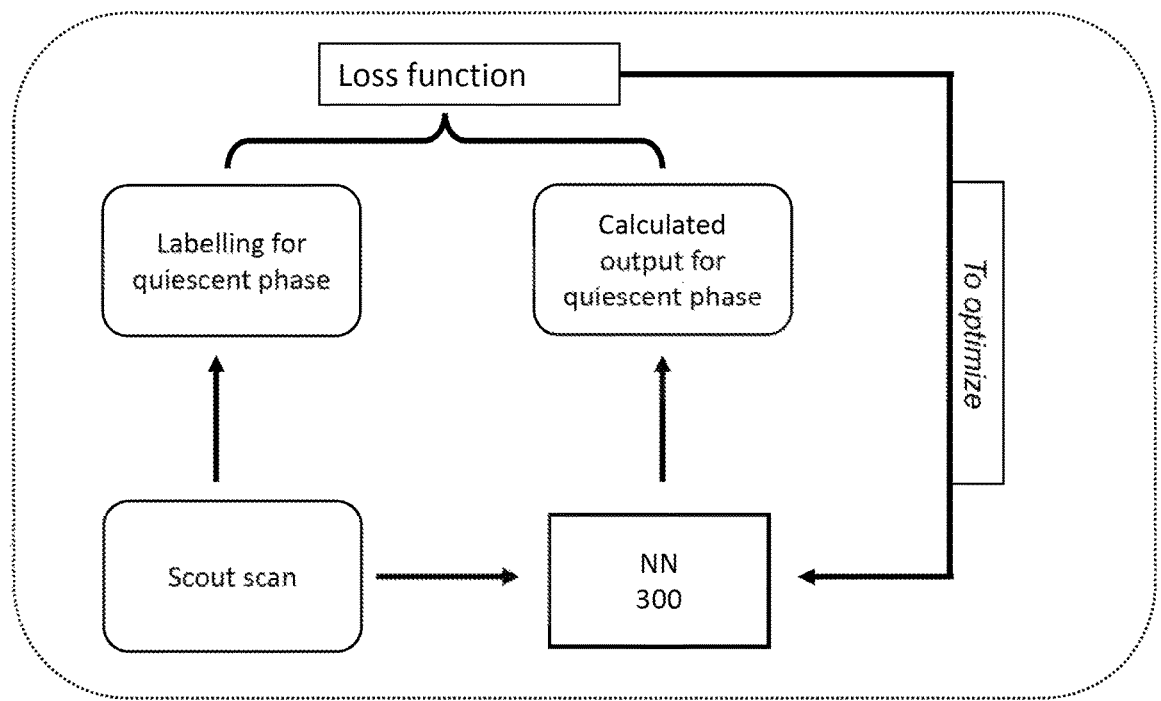
FIG. 8 illustrates a neural network begin trained to act as a phase calculator of FIG. 5.

According to an alternative aspect described herein, the phase calculator is implemented as a neural network 300 as shown in FIG. 8. The neural network 300 can be trained to perform a classification task, where the untrained network is trained with labelling for quiescent phase (and optionally duration) so that it can learn features indicating the quiescent phase (and optionally the duration of the quiescent phase). During the training of the network 300, in FIG. 6A an untrained network is provided 2D scout scan images from a set image data taken from a large number of patients (e.g., 100) and trained to minimize a loss function which matches a labelled result (a result known a priori) with a calculated result. The trained neural network can then be used to identify a quiescent phase from a series of scout scans.

Figure 10:
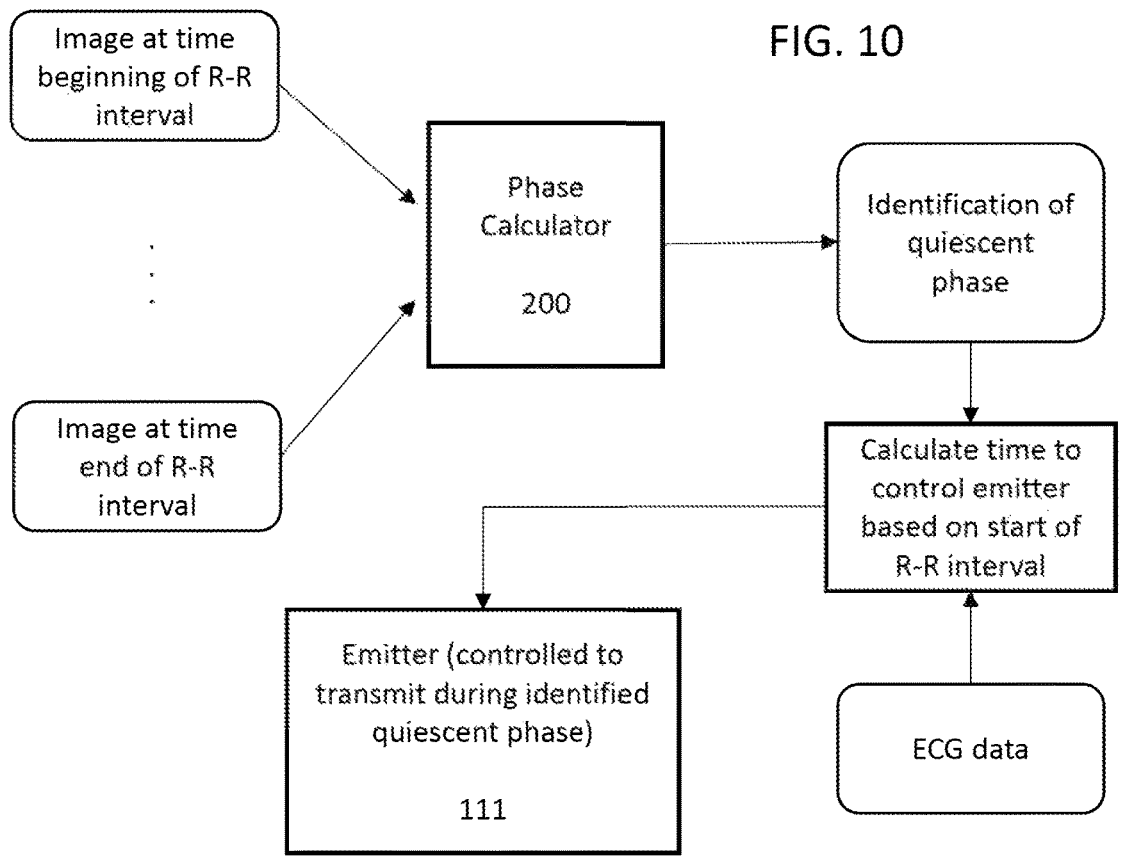
FIG. 10 illustrates processing circuitry configured to determine a quiescent phase to act as an X-ray irradiation period by analyzing scout scan images prior to a diagnostic imaging and performing the diagnostic imaging during the identified phase based on the start of the R-R interval.

Using any of the phase calculators 200 described above, processing circuitry can be used to statically determine a quiescent phase from the scout scan images and correlate the quiescent phase to a start of the ECG signal, during diagnostic imaging, as shown in FIG. 10. The emitters need only emit radiation during the quiescent phase (or over a duration including just before the quiescent phase through just after the quiescent phase) statically determined based on the scout scan, thereby reducing the amount of radiation applied to a patient. The system also may detect whether a quiescent phase appears not to have been accurately determined. For example, when using a cross-correlation calculator, the system may signal that it has failed to find the quiescent phase if it does not find a cross-correlation coefficient higher than a first threshold. Similarly, when using a circularity calculator, the system may signal that it has failed to find the quiescent phase if it does not find a circularity score higher than a second threshold. In either such case, the system instead may use a known technique for determining a quiescent phase, such as using a PhaseXact method of finding a quiescent phase.

Figure 9:
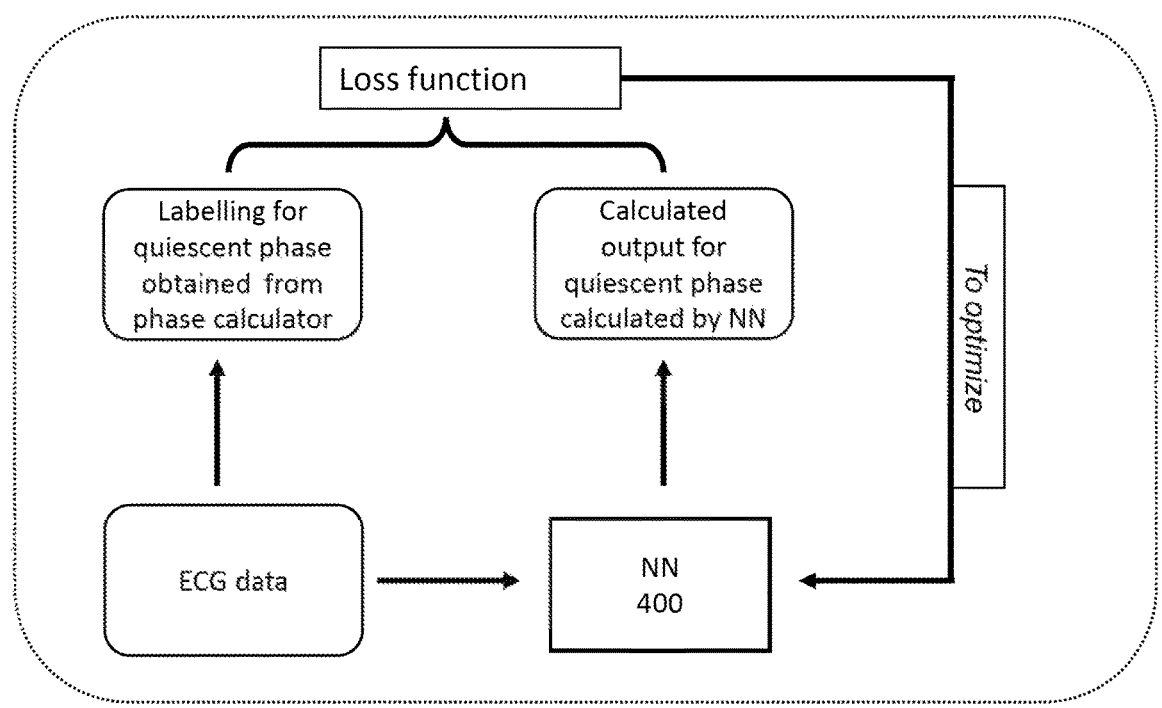
FIG. 9 illustrates the training of a neural network that is trained to determine a quiescent period to act as an X-ray irradiation period associated with an electrocardiogram acquired from an electrocardiography device, by processing the electrocardiogram and an indication of the quiescent period determined from multiple scout CT images acquired, from a scout CT scan, at multiple different cardiac phases.
Figure 11:
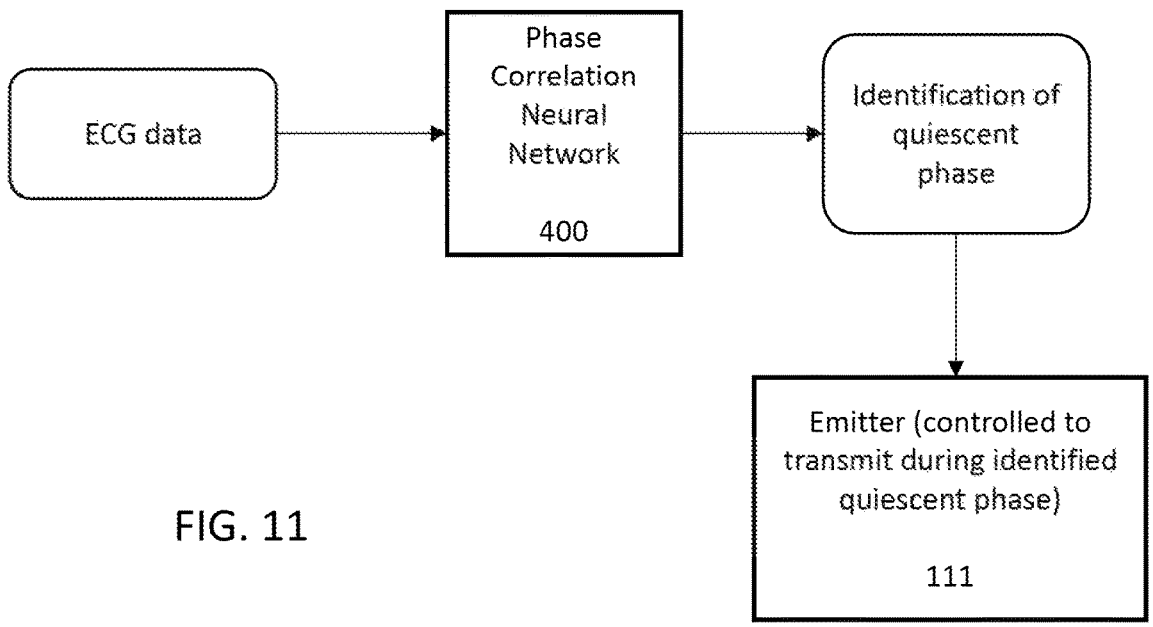
FIG. 11 illustrates a trained neural network determining a quiescent period to act as an X-ray irradiation period by analyzing only an electrocardiogram acquired from an electrocardiography device as would be obtained during diagnostic imaging.

Using any of the phase calculators 200 described above, a correlation neural network 400 can be trained (as shown in FIG. 9) to predict from ECG data obtained in connection with the 2D scout scans how the ECG data correlates to the quiescent phase in patients. By training the correlation neural network 400 to dynamically determine the quiescent phase from the ECG signal, during diagnostic imaging, as shown in FIG. 11, the emitters need only emit radiation during the dynamically determined quiescent phase (or over a duration including just before the quiescent phase through just after the quiescent phase), thereby reducing the amount of radiation applied to a patient. Moreover, because a quiescent phase can be dynamically determined/predicted during diagnostic imaging of the patient from only the ECG data taken during diagnostic imaging, the system can detect whether the quiescent period is changing (e.g., due to a change in heart rate of the patient due to stress). As the quiescent phase dynamically changes, so too can when the x-rays are emitted so that the various views taken during diagnostic imaging are taken when the heart is in the quiescent phase.

In one embodiment of the training of the phase correlation neural network 400, the phase correlation neural network 400 is trained a priori from a patient undergoing an imaging process for diagnostic imaging. In such a configuration, the phase correlation neural network 400 can be trained and embedded within a CT apparatus as a preconfigured phase correlation neural network 400. In another embodiment, the phase correlation neural network 400 is at least partially trained using patient-specific scout scan data and ECG data. For example, a partially trained model is stored in a CT apparatus and may have undergone a large number of training cycles (e.g., 1000 epochs), and prior to diagnostic imaging of patient "P", a scout scan is performed on patient P and the identified quiescent phase and ECG data of patient "P" are added to the training data of the partially trained network. The partially trained network is then further trained for a smaller number of training cycles (e.g., 10-50 epochs) using the identified quiescent phase and ECG data of patient "P" so that the trained network is a personalized phase correlation neural network 400.

As would be appreciated by those of skill in the art, when the phase calculator 200 and the phase correlation neural network 400 are both implemented as a neural network, the two networks can be trained as a single network.

The term "processor" used in the above description, for example, means a circuit such as a CPU, a graphics processing unit (GPU), an application specific integrated circuit (ASIC), and a programmable logic device (for example, a simple programmable logic device (SPLD), a complex programmable logic device (CPLD), and a field programmable gate array (FPGA)). When the processor is, for example, the CPU, the processor performs functions by reading and executing computer programs stored in a storage circuit. On the other hand, when the processor is, for example, the ASIC, the functions are directly incorporated in the circuit of the processor as a logic circuit instead of storing the computer programs in the storage circuit. Note that each processor of the embodiment is not limited to a case where each processor is configured as a single circuit, and one processor may be configured by combining a plurality of independent circuits to perform functions thereof. Moreover, a plurality of components in each drawing may be integrated into one processor to perform functions thereof.

In addition to the embodiments described above, additional embodiments are described in the parentheticals set forth below.

(1) A control method of performing X-ray CT scans, including, but not limited to: determining an X-ray irradiation period from an electrocardiogram acquired from an electrocardiography device attached to a living object to be imaged, by processing the electrocardiogram at multiple different cardiac phases; performing, by controlling a CT gantry including and rotatably supporting an X-ray source and an X-ray detector, a diagnostic CT scan in the determined X-ray irradiation period, of at least a part of the heart region, to obtain a CT image; and causing a display unit to display the obtained CT image.

(2) The method according to (1), wherein determining an X-ray irradiation period from an electrocardiogram comprises applying the electrocardiogram and multiple scout CT images from a scout CT scan to a trained machine learning model trained to correlate a cardiac phase to electrocardiogram signals.

(3) The method according to either (1) or (2), wherein determining an X-ray irradiation period from an electrocardiogram comprises applying the electrocardiogram to a trained machine learning model trained to correlate a cardiac phase to electrocardiogram signals.

(4) The method according to any one of (1)-(3), further including, but not limited to: performing the diagnostic CT scan in the determined X-ray irradiation period for a determined X-ray irradiation period duration.

(5) The method according to any one of (1)-(4), wherein determining the X-ray irradiation period includes, but is not limited to: obtaining multiple scout CT images from a scout CT scan correlated to the electrocardiogram; and calculating cardiac motion related metrics based on the scout CT scan within individual R-R intervals associated with the electrocardiogram.

(6) The method according to any one of (1)-(5), wherein the scout CT scan utilizes lower-dose radiation than the diagnostic CT scan.

(7) A computed tomography (CT) imaging device including, but not limited to: a CT gantry; an X-ray source rotatably supported by the CT gantry; an X-ray detector rotatably supported by the CT gantry; and processing circuitry configured to: determine an X-ray irradiation period from an electrocardiogram acquired from an electrocardiography device attached to a living object to be imaged, by processing the electrocardiogram at multiple different cardiac phases; perform, by controlling the CT gantry, a diagnostic CT scan in the determined X-ray irradiation period, of at least a part of the heart region, to obtain a CT image; and cause a display unit to display the obtained CT image.

(8) The CT imaging device according to (7), further including, but not limited to: the display unit to display the obtained CT image.

(9) The CT imaging device according to (7), further comprising processing circuitry configured to perform any one of the methods of (2)-(6).

(10) A computer readable storage device including, but not limited to, a non-transitory computer readable storage medium for storing computer instructions therein, wherein the computer instructions, when read from a computer memory and executed by a computer processor, cause the computer processor to perform the method of any one of (1)-(6).

(11) A computed tomography (CT) imaging device controller for controlling a CT imaging device including, but not limited to: a CT gantry; an X-ray source rotatably supported by the CT gantry, and an X-ray detector rotatably supported by the CT gantry, wherein the CT imaging device controller includes, but is not limited to: processing circuitry configured to: determine an X-ray irradiation period from an electrocardiogram acquired from an electrocardiography device attached to a living object to be imaged, by processing the electrocardiogram at multiple different cardiac phases; perform, by controlling the CT gantry, a diagnostic CT scan in the determined X-ray irradiation period, of at least a part of the heart region, to obtain a CT image; and cause a display unit to display the obtained CT image.

(12) A method of training an untrained neural network to determine an X-ray irradiation period from electrocardiograms and timings of corresponding quiescent phases, including, but not limited to: repeatedly applying the electrocardiograms and a loss function based on the timings of the corresponding quiescent phases to the untrained neural network until the untrained neural network estimates to within a training threshold the timings of the corresponding quiescent phases from electrocardiograms.

(13) The method of (12), wherein the timings of the corresponding quiescent phases are obtained from multiple scout CT images per multiple scout CT scans correlated to corresponding cardiac phases in corresponding electrocardiogram signals.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A control method of performing X-ray CT scans, comprising:
    determining an X-ray irradiation period from an electrocardiogram acquired from an electrocardiography device attached to a living object to be imaged, by processing the electrocardiogram at multiple different cardiac phases;
    performing, by controlling a CT gantry including and rotatably supporting an X-ray source and an X-ray detector, a diagnostic CT scan in the determined X-ray irradiation period, of at least a part of the heart region, to obtain a CT image; and
    causing a display unit to display the obtained CT image.

2. The method according to claim 1, wherein determining an X-ray irradiation period from an electrocardiogram comprises applying the electrocardiogram and multiple scout CT images from a scout CT scan to a trained machine learning model trained to correlate a cardiac phase to electrocardiogram signals.

3. The method according to claim 1, wherein determining an X-ray irradiation period from an electrocardiogram comprises applying the electrocardiogram to a trained machine learning model trained to correlate a cardiac phase to electrocardiogram signals.

4. The method according to claim 1, further comprising:
    performing the diagnostic CT scan in the determined X-ray irradiation period for a determined X-ray irradiation period duration.

5. The method according to claim 1, wherein determining the X-ray irradiation period comprises:
    obtaining multiple scout CT images from a scout CT scan correlated to the electrocardiogram; and
    calculating cardiac motion related metrics based on the scout CT scan within individual R-R intervals associated with the electrocardiogram.

6. The method according to claim 1, wherein the scout CT scan utilizes lower-dose radiation than the diagnostic CT scan.

7. A computed tomography (CT) imaging device comprising:
    a CT gantry;
    an X-ray source rotatably supported by the CT gantry;
    an X-ray detector rotatably supported by the CT gantry; and
    processing circuitry configured to:
        determine an X-ray irradiation period from an electrocardiogram acquired from an electrocardiography device attached to a living object to be imaged, by processing the electrocardiogram at multiple different cardiac phases;
        perform, by controlling the CT gantry, a diagnostic CT scan in the determined X-ray irradiation period, of at least a part of the heart region, to obtain a CT image; and
        cause a display unit to display the obtained CT image.

8. The CT imaging device according to claim 7, wherein the processing circuitry configured to determine an X-ray irradiation period from an electrocardiogram comprises processing circuitry configured to apply the electrocardiogram and multiple scout CT images from a scout CT scan to a trained machine learning model trained to correlate a cardiac phase to electrocardiogram signals.

9. The CT imaging device according to claim 7, wherein the processing circuitry configured to determine an X-ray irradiation period from an electrocardiogram comprises processing circuitry configured to apply the electrocardiogram to a trained machine learning model trained to correlate a cardiac phase to electrocardiogram signals.

10. The CT imaging device according to claim 7, further comprising processing circuitry configured to perform the diagnostic CT scan in the determined X-ray irradiation period for a determined X-ray irradiation period duration.

11. The CT imaging device according to claim 7, wherein the processing circuitry configured to determine the X-ray irradiation period comprises processing circuitry configured to:
    obtain multiple scout CT images from a scout CT scan correlated to the electrocardiogram; and
    calculate cardiac motion related metrics based on the scout CT scan within individual R-R intervals associated with the electrocardiogram.

12. The CT imaging device according to claim 7, wherein the scout CT scan utilizes lower-dose radiation than the diagnostic CT scan.

* * * * *